United States Patent [19]
Brenn

[11] Patent Number: 5,581,189
[45] Date of Patent: Dec. 3, 1996

[54] WATER PURITY TESTING SYSTEM HAVING REVERSING POLARITY

[76] Inventor: Eric W. Brenn, 171 Greenfield, Irvine, Calif. 92714

[21] Appl. No.: 300,418

[22] Filed: Sep. 2, 1994

Related U.S. Application Data

[63] Continuation-in-part of Ser. No. 974,616, Nov. 12, 1992, abandoned, which is a continuation-in-part of Ser. No. 853,033, Mar. 17, 1992, abandoned.

[51] Int. Cl.$^6$ ................................................ G01R 27/28
[52] U.S. Cl. ................................................ 324/439; 204/402
[58] Field of Search ........................... 324/439, 425; 204/402, 406; 210/748

[56] References Cited

U.S. PATENT DOCUMENTS

| | | | |
|---|---|---|---|
| 3,592,212 | 7/1971 | Schleimer | 137/93 |
| 4,275,448 | 7/1981 | Le Dall | 364/500 |
| 4,496,454 | 1/1985 | Berger | 204/402 |
| 4,504,790 | 3/1985 | Frant | 324/439 |
| 4,705,617 | 11/1987 | Beebe et al. | 204/402 |
| 4,772,375 | 9/1988 | Wullschleger et al. | 204/402 |
| 4,950,378 | 8/1990 | Nagata | 204/406 |
| 5,057,212 | 10/1991 | Burrows et al. | 324/439 |
| 5,059,908 | 10/1991 | Mina | 324/425 |
| 5,162,077 | 11/1992 | Bryan et al. | 204/406 |
| 5,435,894 | 7/1995 | Hayakawa | 204/149 |

Primary Examiner—Maura K. Regan
Attorney, Agent, or Firm—Curtis L. Harrington

[57] ABSTRACT

A water purity testing system includes a sensor housing having an internal chamber within which pair of electrodes are supported. Fittings are provided for coupling the housing to a water supply and introducing water into the chamber. A temperature sensor is supported within the housing. A system processor and control unit is operatively coupled to the electrodes and the temperature sensor and includes a source of voltage DC current measurement which is applied to the electrodes to facilitate the measurement of water conductivity within the housing chamber, followed by a grounding period to provide as settling time to prevent the build-up of debris on the electrodes. The microprocessor also utilizes the temperature measurement during the testing cycle to derive a temperature factored measurement of total dissolved solids within the water under test. A display system is coupled to the microprocessor and is operated under microprocessor control to provide a test result display output. Other uses include a soft water sensor, purity testing system, water level control, and in a probe system for viscous materials.

18 Claims, 7 Drawing Sheets

WATER PURITY TESTING SYSTEM HAVING REVERSING POLARITY

FIELD OF THE INVENTION

This application is a Continuation-in-Part of application entitled LONG-TERM ELECTRICAL CHEMICAL TESTING SYSTEM having Ser. No. 07/974,616, filed Nov. 12, 1992, now abandoned, which was a continuation-in-part of Ser. No. 07/853,033, filed Mar. 17, 1992, now abandoned, by the applicants of the present application which is hereby incorporated by reference.

FIELD OF THE INVENTION

This invention relates generally to water purity measurement and testing and particularly to testing systems using electrical energizing.

BACKGROUND OF THE INVENTION

A great variety of water systems used presently require substantial ongoing water purity and contamination testing. For example, facilities such as municipal water supplies, beverage bottlers or medical facilities often require testing systems to protect the consumer or end user as well as to protect other equipment within the system. Still other systems operative in waste disposal or industrial water utilizing operations may be required to provide water testing of the discharged water as part of environmental monitoring or control operations.

On the one hand, periodic sample extraction and testing enjoys limited acceptance and may be employed in less critical operations, the most reliable practice for water testing and monitoring will use a continuous, or in-line testing system.

In one of the most common in-line testing systems the conductivity of the water or water solution is used an indication of water purity and contaminant content. The basic principle of such conductivity testing is relatively simple in that a pair of metal electrodes are immersed within the water or water solution and coupled to a source of electrical current. As the electrical current travels through the water or water solution between the electrodes, the conductivity or resistance of the water may be readily calculated to provide the desired indication of water purity. This conductivity testing has been found to yield excellent results and has wide scientific acceptance. Despite the great promise and advantages of such conductivity testing systems, several practical limitations and problems arise which has thus far precluded full realization of the benefits. Perhaps the most serious limitation and problem set arises due to the electrolytic properties of so-called aqueous solutions (solutions of water contaminated with mineral or metal materials or compounds). This set of properties is well known and arises when water-based solutions typical of virtually all water systems are subjected to electrical current between immersed electrodes. As the electrodes are energized, metal and mineral elements or other contaminants become ionized or charged and are carried to one or the other of the electrodes. At the electrode, the ionized or charged particles formed electrode deposits which over time coat and erode the electrodes reducing their efficiency and eventually rendering them useless. In addition, the coating or depositing action upon the electrodes often obstructs the water flow about the electrode and in certain structures may constrict the monitored water flow.

In efforts to meet these problems, practitioners in the art have employed exotic metal electrodes such as titanium, platinum, or carbon which tend to be less electrochemically active. Practitioners have also recommended frequent replacement of electrodes as well as the use of larger electrodes and AC current. An additional approach often tried is the provision of extra electrodes forming so-called sacrificial electrodes. Despite some limited improvement, such approaches have failed to provide the desired performance and reliability of electrical water testing systems.

The measurement of purity is a more subtle process than a simple measurement of conductivity. Purity measurement involves a more sensitive conductivity measurement, which may not be present in other measurement systems. For example, U.S. Pat. No. 3,474,330 to Thomas M. Dauphinee, which issued on Oct. 21, 1969 and is entitled "Conductivity Measuring Apparatus with Means for Comparing Sampled and Reference Voltages," discloses the use of a sensor and method which may operate up to a mile away from the measurement devices which operate the sensor. A sample cell is suspended in sea water from a ship, and water is allowed to move through the sample cell as the ship moves. In that case the utilization of DC current measurement was avoided for polarization effects, and AC current rejected due to the reactive interactions in the cable, phase problems and inability to accurately measure output over a long distance. The solution was the use of a square wave to provide and charging capacitors to measure the voltage average.

This technique may be adequate for sea water especially due to the long extension of equipment and the specialized probe employed. The problem occurs, which has heretofore been solved in the presence of multiple ground taps, as is encountered in conventional equipment. If a simple square wave device is used in such equipment, the grounding problems can alter the square wave. This, in turn will easily change the readings and most likely cause an unbalanced wave that can erode or plate the electrodes. Another problem with a simple square wave technique is that it is taking an average reading of the square wave voltages from the resistor and cannot use formulas developed and proven for actual reading using DC current measurement. Taking an average reading is not as accurate as taking an actual reading. Another problem with the technique is that depending on what frequency rates you use and the nature of the elements that are suspended in water, the phenomenon of frequency resonation can occur which can effect the average reading as well as the electrodes. It can also effect other monitoring or processing equipment connected to the distribution line. Any constant, continuously generated square wave form which does not exactly balance will tend to, on average, polarize the electrodes and cause problems.

The problems may range from electrochemical effects where one electrode has its metal ions dissolved into the surrounding water, to a chemical compilation of species in the water which collectively layer onto one or both electrodes. Even without a chopped signal, and where a completely regulated square wave can be provided, this signal can fall out of calibration. In fact, over time, one additional electron supplied to one electrode over the other per cycle can cause a major charge buildup.

There remains, therefore, a continuing need in the art for evermore improved water purity testing systems which exhibit greater reliability, longer electrodes and which avoid interfering with the primary water flow of the system, and which will defeat any buildup of charge or net charge presence on one electrode over another.

SUMMARY OF THE INVENTION

Accordingly, it is a general object of the present invention to provide an improved water purity testing system. It is a more particular object of the present invention to provide an electrically operated water purity testing system which exhibits longer electrode life, more reliable test results and which avoids interfering with the water flow through the testing system.

In accordance with the present invention, there is provided for use in testing water for dissolved solids, a water testing system comprises: a housing for receiving the water having a test chamber defined therein; a pair of electrodes supported by the housing exposed to the water within the test chamber; means for applying a first DC current measurement to the electrodes in one direction through the electrodes, and then grounding the electrodes, and then applying a second DC current measurement in the other direction to the electrodes, and grounding the electrodes. Grounding takes place either with respect to another structure, or if none is available, to each other or the sample.

It is this grounding step which absolutely prohibits a net charge from building up on either electrode, or for that matter on any associated structure. If an associated structure is capable of becoming charged by virtue of action of the electrodes, it will be similarly capable of becoming discharged by grounding the electrodes.

The invention uses settling time, the time needed for the metal to return to its original state, to insure equilibrium. This allows the molecules to bond and lets the capacitance, magnetic and other after effects of electrical currents travelling through metals to settle before a further current is passed through again. This assists in the balancing because the next cycle, regardless of how the cycle is defined, can start at a state as closely as possible to zero.

Using the relays and measuring the voltage, it is found that duplicate signals are sent accurately through the sensor in two directions, first in one direction then the other. For balanced operation, the rise times, spikes, et cetera will be duplicated in both directions in the sensor. In addition, the zero state can occur between each DC current measurement, after a pair of oppositely going DC current measurements, or after any preset number of DC current measurements.

Both the settling time and the balancing act of the electronics circuit enable the device of the invention to have success in being able to withstand the electrolysis and other effects usually associated in this field.

Another way the operation can be visualized is to consider a single metal ion which is sent back and forth between the electrodes. Where a balanced electrolysis is used, the electrolysis will typically be confined to the small ion first displaced and then returned to its place.

BRIEF DESCRIPTION OF THE DRAWINGS

The invention, its configuration, construction, and operation will be best further described in the following detailed description, taken in conjunction with the accompanying drawings in which.

DETAILED DESCRIPTION OF THE PREFERRED EMBODIMENT

Figure 1:
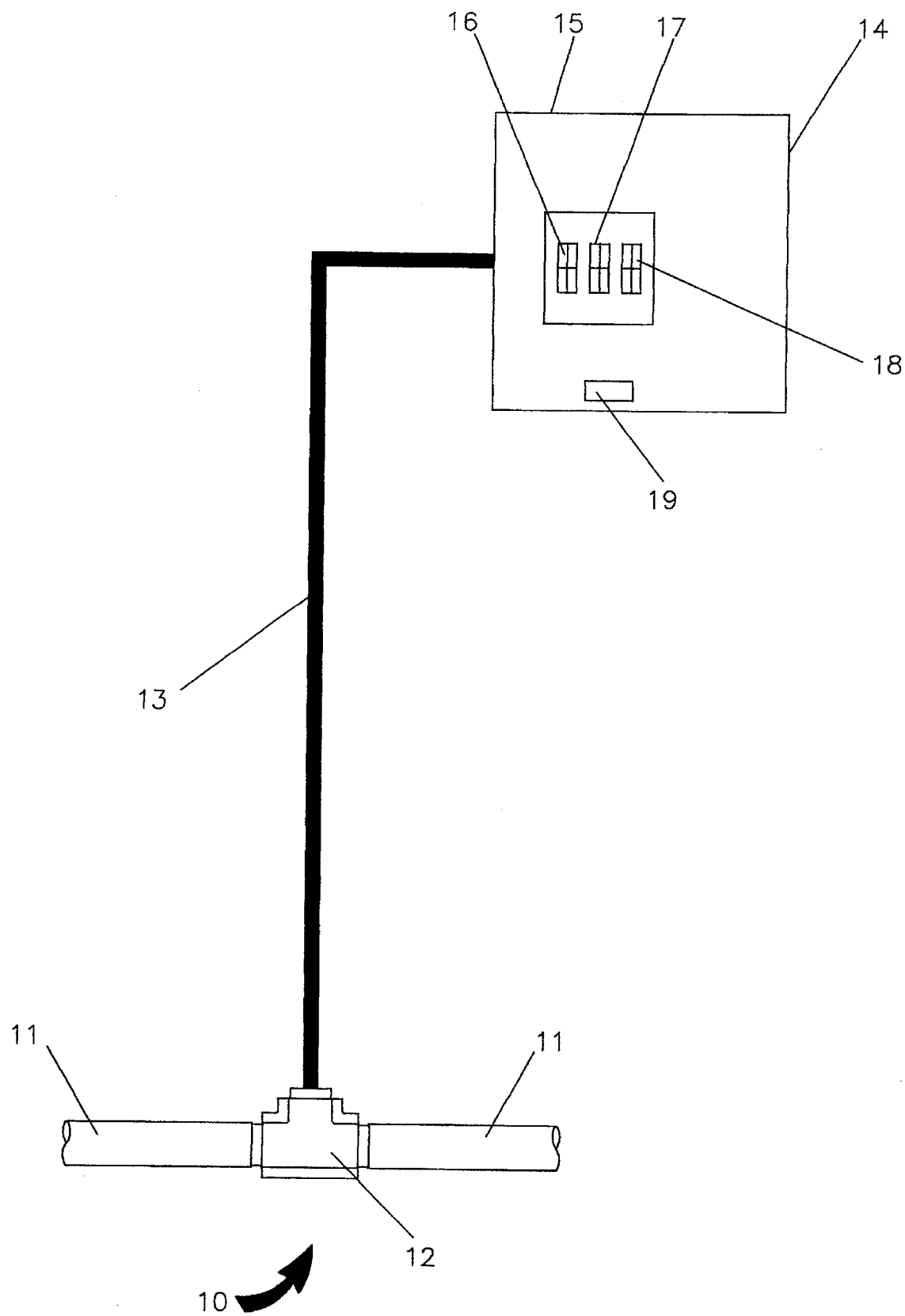
FIG. 1 sets forth a block diagram of the present invention water purity testing system.

FIG. 1 sets forth a generalized block diagram of a water purity testing system constructed in accordance with the present invention and generally referenced by numeral 10. Water purity testing system 10 is coupled to a conventional water supply or water carrying apparatus 11. A sensing unit 12 is inserted between elements of water supply conduit 11 and thus as is set forth below in greater detail provides a coupling path through sensing unit 12 to facilitate water purity testing. A system processor and control unit 14, the details of which are set forth below, include a system processor and electrical control (seen in FIG. 2) which are coupled to sensing unit 12 by a plurality of coupling lines 13. System processor and control 14 further includes a display readout 15 having plurality of digital display segments 16, 17 and 18 together with a user accessible test button 19.

In operation and by means set forth below in greater detail, system processor and control 14 applies a succession of DC current measurements, preferably of alternating directions, to electrodes within sensing unit 12 via coupling lines 13. As is also set forth below in greater detail, the electrical conductivity or resistance offered by the water within sensing unit 12 is measured to provide an indication of the dissolved matter content within water supply conduit 11. In addition, a temperature sensor within sensor unit 12 (not seen in FIG. 1, but which will be discussed more fully with respect to FIG. 2) provides a temperature signal which is coupled to system processor and control 14 via coupling lines 13. System processor and control 14 utilizes the conductivity measurement results together with the temperature signal to derive a numeric value for total dissolved solids within water supply conduit 11 and to produce a corresponding display using segments 16 through 18 on display readout 15.

As is set forth below in greater detail, system processor and control 14 includes an internal timer which periodically activates the testing system and carries it through a cycle to derive the desired measurements which are displayed and stored within an internal memory. This is beneficial because it limits the duty cycle of the device of the present invention, but insures that an adequate number of measurements will be made. The number of measurements can be controlled based upon a predetermined frequency of sampling, or upon the speed with which the measurements change. In addition, test button 19 may be utilized at any time to interrupt system operation and provide an immediate reading by initiating a testing cycle and display of the results thereof. In accordance with an important aspect of the present invention set forth below in greater detail, testing system 10 utilizes alternating DC current measurement the energizing and sensing unit 12 to balance out or negate the tendency of the testing system to accumulate the above-described electrolytic deposition of materials upon the system electrodes. The use of temperature related information in determining the dissolved solids readout value of the present invention system increases system accuracy.

Conductivity measurement utilizing a DC current measurement in grounded equipment is one of the ways to get a very accurate measurement. In order to overcome the polarization, electroplating, erosion, electrolysis and other problems, the present invention utilizes two independent conductivity measurements of DC current. The present invention takes a DC conductivity measurement, then pauses, allows polarization and other effect to clear from the electrodes. Then the invention takes another DC conductivity measurement, the opposite directions and then pauses again. This cycle gives an accurate water reading and the electrolysis and other effects are kept in control because the DC conductivity measurement is balanced and the electrolysis and other effects are reversed. After one cycle the unit returns back to the original state without the normal problems associated with a DC conductivity measurement.

Since there are two DC conductivity measurements, one of the readings is thrown out because it only needs one to make the calculation. One of the readings is merely used to balance the electrolysis effects. The proven industry standardized formulas with which the invention may be used are as follows.

$$DM/(1+A*(TM-TC))=DC \quad (1)$$

where:
A=Alpha of the sample water expected, a number which varies from 0–1. The average for drinking water is A=0.02
DM=TDS at the unit is reading
DC=TDS that is temperature compensated
TM=TEMPERATURE that the unit is reading
TC=TEMPERATURE of 25 degrees C.

Other formulas which work in conjunction with the above equation includes the formula for calculating the TDS at the unit:

$$DM=EXP^{(-2.209*(Vin)+9.274)}$$

where EXP stands for natural exponent e, the inverse of Ln, the natural log. The formula for calculating the TEMPERATURE at the unit may be somewhat dependent upon the equipment, but the following range, shown in Table 1 is typical.

TABLE 1

| Voltage IN Ranges | Formula to Use |
|---|---|
| 0 V–1.11 V | TM = –36.36 * Ln * (Vin/5.05) |
| 1.11 V–1.64 V | TM = –28.57 * (Vin) + 86.87 |
| 1.64 V–2.31 V | TM = –22.22 * (Vin) + 76.46 |
| 2.31 V–2.97 V | TM = –22.618 * (Vin) + 77.151 |
| 2.97 V–3.77 V | TM = –12.029 * (Vin) * (Vin) + 50.122 * (Vin) – 32.846 |
| 3.77 V–4.01 V | TM = –97.247 * (Vin) * (Vin) + 694.49 * (Vin) – 1251.1 |
| 4.01 V–5 V | TM = –388.99 * (Vin) * (Vin) + 3042.2 * (Vin) – 5974.2 |

Here, (Vin) represents the voltage input from ADC in decimal form. Note that the numbers in formulas may change depending on the size of the electrodes used and their distance apart. The numbers and formula of the temperature change depends on the different types temperature sensors used.

Figure 2:
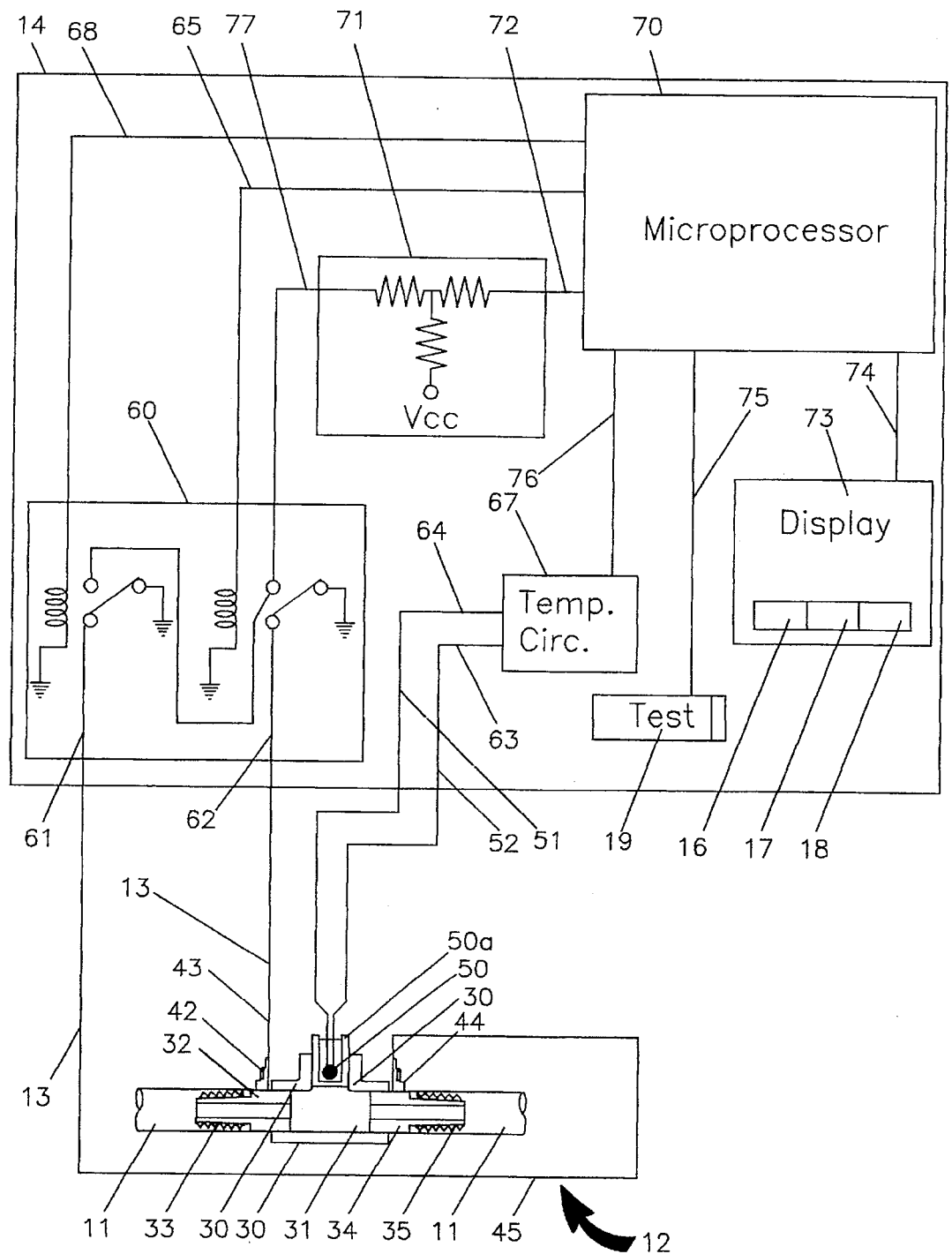
FIG. 2 sets forth a more detailed block diagram of the present invention water purity testing system in which the sensing unit is shown in section view.

FIG. 2 sets forth a block diagram of the present invention testing system together with a sectional view of sensing unit 12. As described above, sensing unit 12 forms a portion of the conduit of a water supply system 11. In this example, water supply conduit 11 comprises a flow pipe or other conduit from which a small segment has been removed, and between which the sensing unit 12 is inserted. Thus, the system flow through water supply conduit 11 also travels through sensing unit 12. More specifically, sensing unit 12 includes a sealed housing 30 defining an interior chamber 31. The sealed housing 30 is preferably an insulator, which insulates with respect to the water supply conduit 11 as well as other conductive structures within the sealed housing 30. A pair of electrodes 32 and 34 are secured to housing 30 by conventional fastening means such as threaded or other attachment.

A pair of outwardly extending fittings 33 and 35 extend from electrodes 32 and 34 respectively and are operative to couple sensing unit 12 to water supply conduit 11 on either side of housing 30. A pair of electrical connectors 42 and 44 are electrically coupled to electrodes 32 and 34 respectively to provide electrical connection to the electrodes. As shown in FIG. 2, electrodes 32 and 34 are formed of flow conduit portions, although this is not a requisite of the present invention. Such a structure does, however help to provide an electrode surface whose area is relatively extended.

A temperature sensor 50 is constructed in accordance with conventional fabrication techniques which may, for example, comprise a conventional thermocouple capable of producing a temperature indicative signal is secured to housing 30 in accordance with conventional fabrication techniques.

A system processor and control device is shown within the boundary line 14, which is the system processor and control unit 14, includes an electronic switching system, interface, or other similar unit 60 having a pair of input/output connections 61 and 62 coupled to connectors 42 and 44 respectively by wires 43 and 45. The electronic switching system 60 is shown in its most extremely simple configuration as a relay for ease of understanding with respect to FIG. 2. The electronic switching system unit 60 is coupled together to the microprocessor 70 by connections 68 and 65.

The Temperature sensor 50 is typically a thermocouple which is encased within a thermally conductive collar 50A. The system further includes a temperature circuit 67 coupled to a input/output connectors 63 and 64 respectively by wires 51 and 52. A microprocessor 70 and a DC current generation circuit 71 constructed in accordance with conventional fabrication techniques is connected by line 72. The DC current generation circuit 71 is also connected to the electronic switching system 60 by line 77. An optional display unit 73 includes conventional circuitry for responding to microprocessor 70 input signals and producing corresponding energizing signals for a plurality of digital display segments 16, 17 and 18 which form readout 13. A test button override 19 is coupled to microprocessor 70.

In operation, microprocessor 70 and interface 60 function in accordance with the system operation set forth below in the flow diagram of FIG. 3 to periodically implement a water purity test cycle which culminates in the optional display upon display 73 of the test results. Alternatively, the test results can be stored for later readout. In addition, the actuation of the test button 19 causes an immediate implementation of a water purity test cycle and display of results upon display 73, to enable operator inspection of the device of the present invention at any time.

More specifically, the DC current generating circuit 71 may include the ability to sense voltage or current and send those results back to the microprocessor 70. In accordance with the system operation set forth below, microprocessor 70 configures electronics switching system 60 to enable the DC current measurement to take place across to electrodes 32 and 34 and vary any parameter, such as magnitude, duration, timing, and the grounding of the electrodes 32 and 34 with respect to each other or with respect to the water supply conduit 11. The microprocessor 70 controls these operations by enabling or disabling lines 68 and 65 that connect the microprocessor 70 and electronic switching system 60. In its simplest form, the DC current measurement circuit 65 may include relays to control the time duration that the electrodes 32 and 34 have DC current running through and the direction controlled by microprocessor 70. The resulting application of DC current measurements on electrodes 32 and 34 produces an electrical current through the water within chamber 31 which is measured by the amount of current and voltage used, along with the use of by microprocessor 70, to measure and calculate the conductivity or resistance of the water in accordance with conventional testing techniques.

In accordance with an important aspect of the present invention described below, microprocessor 70 configures the electronic switching system 60 to alternate the direction of the DC current measurement applied to electrodes 32 and 34 on alternate DC current measurement cycles. Thus, the tendency of contaminating deposit formation upon electrodes 32 and 34 is minimized due to the restoring effect of the reversal of the DC current measurement of electrodes 32 and 34.

During each testing cycle, microprocessor 70 reads the temperature of the water under test within chamber 31 using the output signal of temperature sensor 50 through the temperature circuit 67. The Microprocessor 70 receives the test result signals from the connection 76 from the temperature circuit. Microprocessor 70 then functions in accordance with the following diagram set forth below to periodically store the measurements for conductivity and temperature within memory inside the microprocessor 70. The programming within the microprocessor 70 may include a look-up table having a plurality of dissolved solid values and water temperatures together with corresponding temperature weighted dissolved solid values, or may compute the temperature in accordance with a mathematical function. Thus, microprocessor 70 may complete each cycle by identifying the temperature which may then be stored within memory inside the microprocessor 70 and displayed upon display 73.

It will be apparent to those skilled in the art that the present invention system offers substantial advantages not realized by prior art devices. For example, the use of the accuracy of DC current measurement, the switching of electrodes 32 and 34, and inducing settling times by grounding the electrodes greatly minimizes the material buildup or deposition upon the electrodes. As a result, the interference with water flow through the host water system is virtually eliminated. In addition, the usable life and accuracy of electrodes 32 and 34 is greatly increased over prior art systems. Also, electrodes 32 and 34 may be fabricated of lower cost metals such as copper or brass thereby reducing manufacturing costs.

Figure 3:
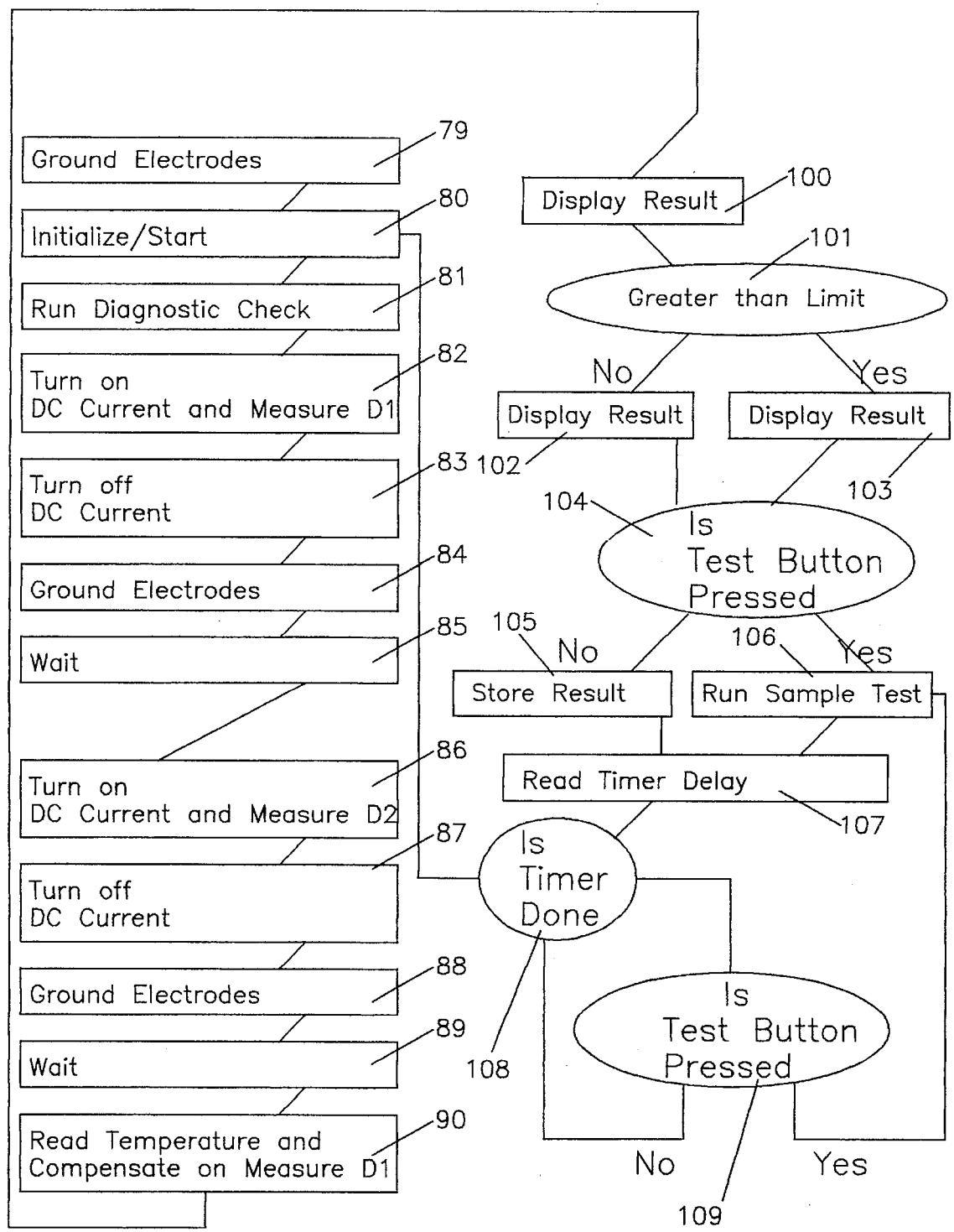
FIG. 3 sets forth a flow diagram of the operation of the present invention water purity testing system.

FIG. 3 sets forth a flow diagram of but one possible mode of the operation of microprocessor 70 and electronic switching system 60 (seen in FIG. 2). In the configuration shown, the system begins at the electrodes 32 and 34 being grounded to system ground step 79 when the system is off or just beginning. The system ground is shown by the ground arrows within the perimeter of switching system 60, and may also connect with the ground connection of other components of FIG. 2. Then the system moves to the initializing step 80 from which it moves to a diagnostic check operation step 81. During the diagnostic check, the system is examined for basic operational capability such as continuity of electrical connections to electrodes 32 and 34 as well as temperature sensor 50 (seen in FIG. 1). Upon successful completion of the diagnostic check at step 81, the system moves to step 82 in which the testing cycle is entered by application of DC current measurement through the electrodes. In response to the applied DC current measurement, which in their preferred form comprise short duration just enough to measure the DC current accurately through the electrodes 32 and 34. The system moves to turn off the DC current step 83 and then grounds the electrodes step 84. The next move is a wait step 85 for the reactions to settle. Usually, this time is close to the same time that the DC current has been travelling through the electrodes 32 and 34.

Optionally, the logic flow may proceed to step 84, the GROUND ELECTRODES step in which the electrodes 32 and 34 are grounded with respect to each other and possibly another electrical potential. For example, and where the conduit 11 is metallic, both the sections of conduit 11 may be connected together and made available for grounding the electrodes 32 and 34. This grounding possibility is indicated at the end of the step of applying the DC current measurement 82, as well as a subsequently applied DC current measurement of opposite direction through the electrodes to emphasize that the steps may be accomplished in any order. The step 82 may apply a DC current measurement of either direction, which is to say that electrode 32 may be positive with respect to electrode 34 or vice versa.

Further, the electrode 32 may be brought to a positive voltage while the electrode 34 either remains at a zero potential, remains at the potential of the conduit 11, or takes on a negative potential. Since the measurement of interest is the potential between the electrodes 32 and 34, a manipulation of the potential of the other surfaces can be accomplished to achieve other purposes.

Thereafter, the system moves to step 86 in which the DC current measurement reversed from that utilized in step 82 after which the reverse DC current measurement is taken to the electrodes. This reversal step 86 may or may not occur during the ground electrodes step 84. During step 86, while the voltage potential is present and current is traveling through electrodes 32 and 34, the system again undertakes a measurement of sample water resistance and total dissolved solids at step 86, the results of which may be stored within the microprocessor memory at step 86. Usually one of the two measurements taken either from step 86 or step 82 is used in the calculations. The other DC current measurement is used to return the effects of the first DC current measurement.

A second opportunity for grounding the electrodes occurs at a GROUND ELECTRODES step 88. It is understood that the grounding of the electrodes may occur at steps 84, 88, or both 88 and 84. As before, the grounding may take place with respect to the electrodes 32 and 34 only, or with respect to the conduit 11, or some other source of ground. Assuming the electrodes 32 and 34 are grounded at step 88, the resistance value computed may be stored, as previously mentioned at step 88. It is understood that the storage of the resistance may occur after any storage step, or indeed anywhere in the flow of logic. Then the system waits at step 89 for the electrodes to settle, again this time can be approximated as the amount of time the electrodes have been active and not given a rest or time to settle. It is understood that this waiting time period of steps 85 and 89 can be placed at different steps and different lengths as long as they come before the repeating step of a DC current measurement already taken and no settling time has been given after it.

The system then senses and reads the temperature of sampled water and calculates any temperature compensation if needed at step 90 and moves to a look-up step 100 in which the microprocessor memory look-up table is read to derive the corresponding temperature factored total dissolved solids reading for the temperature read at step 90. During this look-up process, the electrode metals are allowed to return to the natural state as the energizing charge dissipates. The temperature factored total dissolved solid number derived at step 100 is compared to a predetermined limit at a comparison step 101. In the event the measured total dissolved solid precedes the predetermined limit, the system moves to step 103 and displays a corresponding result. If, however, the limit is not reached at step 101, the system moves to an alternate display step 102 in which a corresponding display is produced.

Following step 102 or 103, the system moves to a decision step 104 in which a determination is made as to whether the test button has been actuated. In the event the test button has been actuated, the system moves to a predetermined short interval delay of approximately fifty seconds in which it will run a sample test step 106 following which the system moves to a read timer step 107.

In the event it is determined at step 104 that the test button has not been actuated, the system moves to a step 105 in which the temperature factored total dissolved solid result obtained at step 100 is stored within the microprocessor memory. Following step 105, the system moves to read timer step 107. Once the timer has been read, the system moves to a decision step 108 in which a determination is made as to whether the system timer has "timed out" or finished a time interval cycle. While the time selected for test interval cycling is, to a large extent, a matter of design choice, it has been found appropriate in the present example to utilize a time interval of approximately three hours. However, it will be recognized by those skilled in the art that virtually any time interval may be selected without departing from the spirit and scope of the present invention.

If at step 108 a determination is made that the system timer has not yet completed the predetermined cycle time, the system moves to a step 109 at which a determination is made as to whether the test button has been actuated. If it is found that the test button has been actuated, the system moves to step 104 and a testing cycle is initiated in response to the test button actuation. If, however, it is found at step 109 that the test button has not been actuated, the system returns to read timer step 107. Thus, in the absence of test button actuation, the system will cycle through step 107 and 108 until the timer has completed its timing interval at which point a determination is made at step 108 that the timer has timed out and a new test cycle is required. Accordingly, the system moves from step 108 to initialize and start step 80 to again commence the full system operation including the running of diagnostic check at step 81.

Further, it is understood, that the timing, order of occurrence and length of occurrence of each of the steps of the present invention can be varied by programming. Thus the DC current, voltage, and duration, and the grounding and length of time which grounding occurs is fully adjustable. Indeed, the electrodes 32 and 34 may remain grounded during the three hour wait for a next cycle.

To explore some of the possibilities, the cycles may occur as follows, with respect to any electrode. DC current measurement it is assumed that conductivity is measured. Direction one (from electrode 32 to 34), direction two (from electrode 34 to 32), grounding; or direction one, grounding, direction two, grounding; or direction two, direction one, grounding; or direction two, grounding, direction on, and grounding. Remember that the duration of any step is fully variable, and the grounding times may extend for hours. Further, an ungrounded rest state may occur between, before or after any and all of the steps set forth above.

Thus, in accordance with the present invention, the testing system shown is operative to undertake a periodic test cycle in response to a basic interval timer or in response to a test button actuation. The measurement cycle itself comprises the application of a DC current measurement to the measuring electrodes in one direction followed after which the direction of the DC current measurement signal is reversed as to electrodes 32 and 34 and again applied to the electrodes to produce a second measurement of resistance, voltage, and current drain that can be measured to accurately find the amount of total dissolved solids, salinity, ohms per square foot, and other measurement classifications whose origins are measurements of particles that are suspended in solution. Upon completion of the alternating DC current measurement portions of the cycle, the temperature is sensed and the results of one of the two measurements, or both together with temperature are utilized by the microprocessor to produce a temperature factored or temperature weighted total dissolved solids measurement. The system also responds to test button actuation to immediately initiate a measurement cycle regardless of timer condition which provides the user with an immediate measurement readout.

The present invention system use of DC current measurement, grounding, and settling times greatly reduces and, in some instances, virtually eliminates the buildup of deposited material upon the measuring system electrodes. As a result, the accuracy and reliability of measurement is maintained for an extended period of time. The electrode life realized in the present invention system is greatly extended beyond that available in the prior art systems and thus system downtime, maintenance costs and repair is greatly reduced. In addition to advantages of reliability and electrode life, the present invention system permits the use of electrodes fabricated of more economical and conventional metals such as copper, brass or the like. Finally, the minimizing of the deposit formation upon the electrodes permits the fabrication of an electrode structure which includes the fittings or couplings used to couple the sensing unit to the water supply system being examined. Thus, the system electrodes may employ conventional tube type insertion fittings or hose fittings or threaded couplers of the type used in pipe fittings as well as other types of fitting structures which substantially reduces the costs associated with removing and installing the sensing unit. The electronic switching system (electronic switching system 60 in FIG. 2) utilized conventional switching circuitry which responds to microprocessor 70 to alternate and control the DC current measurement direction or grounding of DC current coupling to the system electrodes. For example, the electronic switching system 60 may utilize conventional relays or electronic switching circuits fabricated in accordance with conventional switching techniques.

Figure 4:
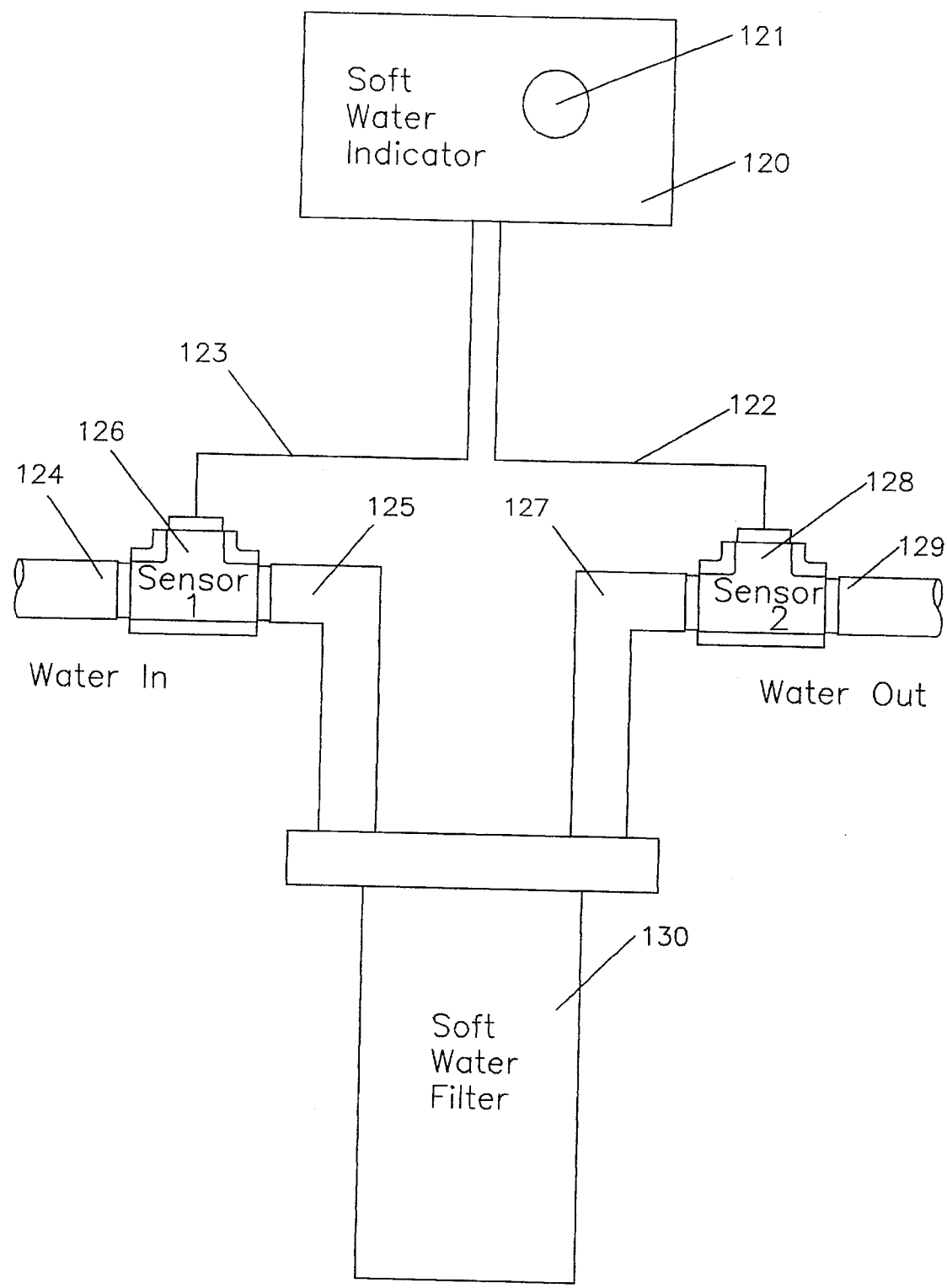
FIG. 4 sets forth one possible configuration in which the present invention is used in conjunction with a soft water indicator.

The invention herein is also especially useful as a soft water sensor. FIG. 4 sets forth a generalized diagram of the water purity testing system working as a soft water or ion exchange indicator in its most basic configuration. The soft water indicator is generally referenced by numeral 131. The soft water indicator uses two sensors 126 and 128 which are connected to the electronics box 120 by wires 122 and 123. The soft water filter or other types of fluid altering filter in other than soft water filter 130 is located between the two sensors 126 and 128 which are connected to the soft water filter 130 by water lines 125 and 127. Incoming water for testing arrives through water line 124 and travels into sensor 126 and then travels through water line 125 into the soft water filter 130 and exits out water line 127 and travels into sensor 128 and then through water line 129 to where it is used. The soft water indicator 120 displays the results of the tests on display 121.

The system operates in the same manner as the water purity testing system except that it uses two sensors 126 and 128 to indicate a difference in DC current measurement between the water that travels into the filter and that water that exits the filter. The filter induces changes in the water chemistry that can be sensed by a difference in DC current measurement between sensors 126 and 128 and that change can then be indicated on the display 121. It is understood that sensors 126 and 128 can be switched or reversed and that the locations of the different components can be changed and varied.

Figure 5:
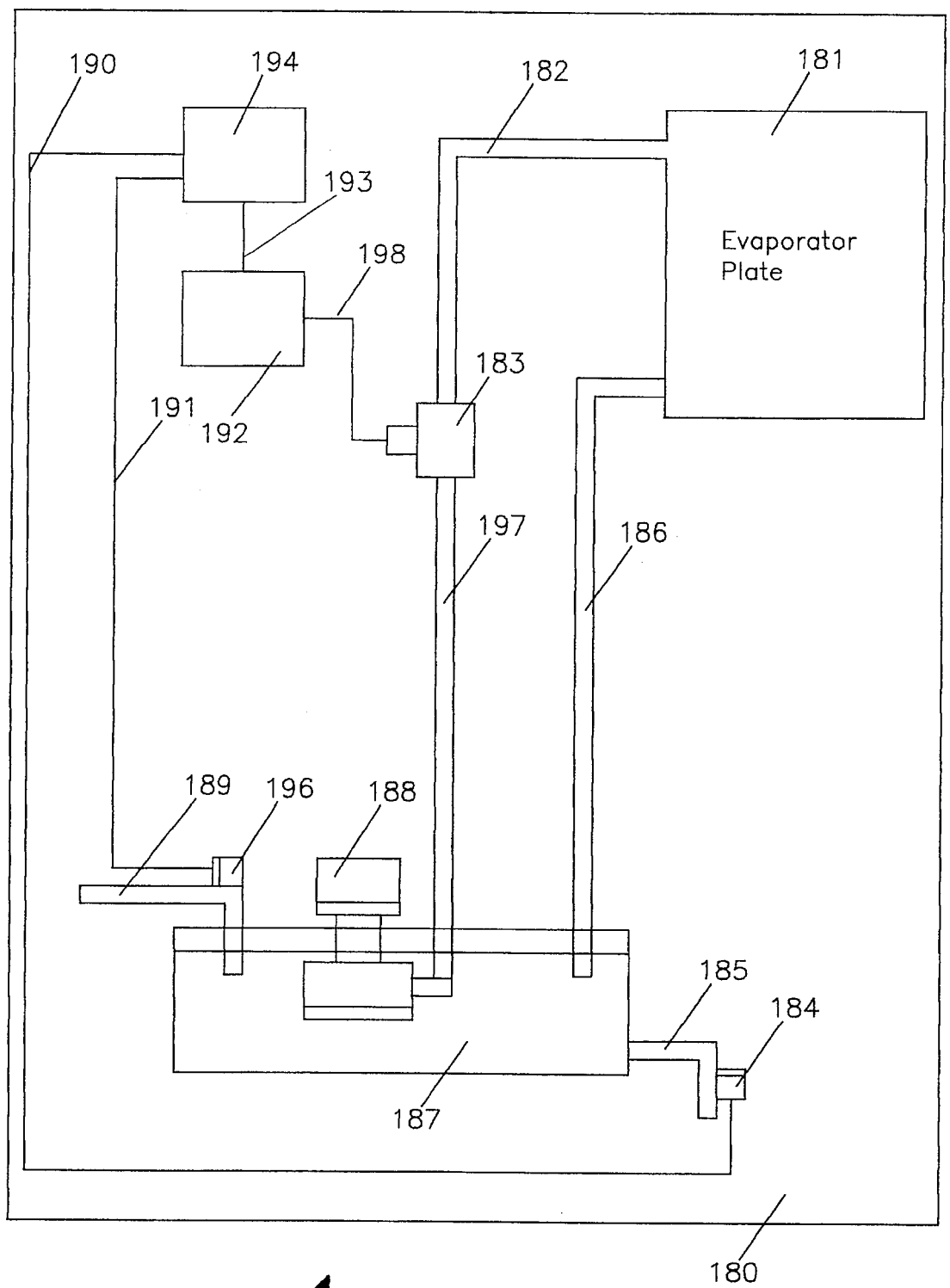
FIG. 5 sets forth one possible configuration in which the present invention is used in conjunction with an ice machine.

The invention herein is also easily adaptable for use as an ice machine flush cycle indicator. FIG. 5 sets forth a generalized diagram of the water purity testing system working as an ice machine flush cycle indicator in its most basic configuration. The flush cycle indicator is generally referenced by the numeral 195. The whole system is usually enclosed inside the ice machine labeled 180. The ice machine controller board or boards 194 and the water purity testing system circuit board 192 is connected by wire 193 in order to access to different aspects of the ice machine functions. The ice machine controller board 194 is connected to the sump drain valve 184 by wire 190 and to the sump fill valve 196 by wire 191 and to many other ice machine functions. These two valves control the water in and water out of the ice machine. The sump drain valve 184 is connected to the sump drain pipe 185 and the sump fill valve 196 is connected to the incoming water line 186 and both are connected to the ice machine sump or reservoir 187, where water can be cooled and stored. The sump pump 188 pumps the water through the pipe 197 then through the sensor 183 and back through the pipe 182 to the evaporator plate 181 and from there the water drains back to the sump via pipe 186. The sensor is connected to the water purity testing system circuit board by wire 198.

As particles and contaminants build up in the system the DC measurement current changes and at specific levels the ice machine can be told to open and close valves 184 and 196 to bring in new water and drain old water and bring down the levels of contamination. It is understood that the locations of the different components can be changed and varied. Also, it is understood that pH probes and other measuring devices including devices that can automatically add chemicals can be added in combination with the current invention. Also, it is understood that the invention can be used in applications in chiller towers, boilers, pools and other applications that need water purity/contamination control and regulation.

Figure 6:
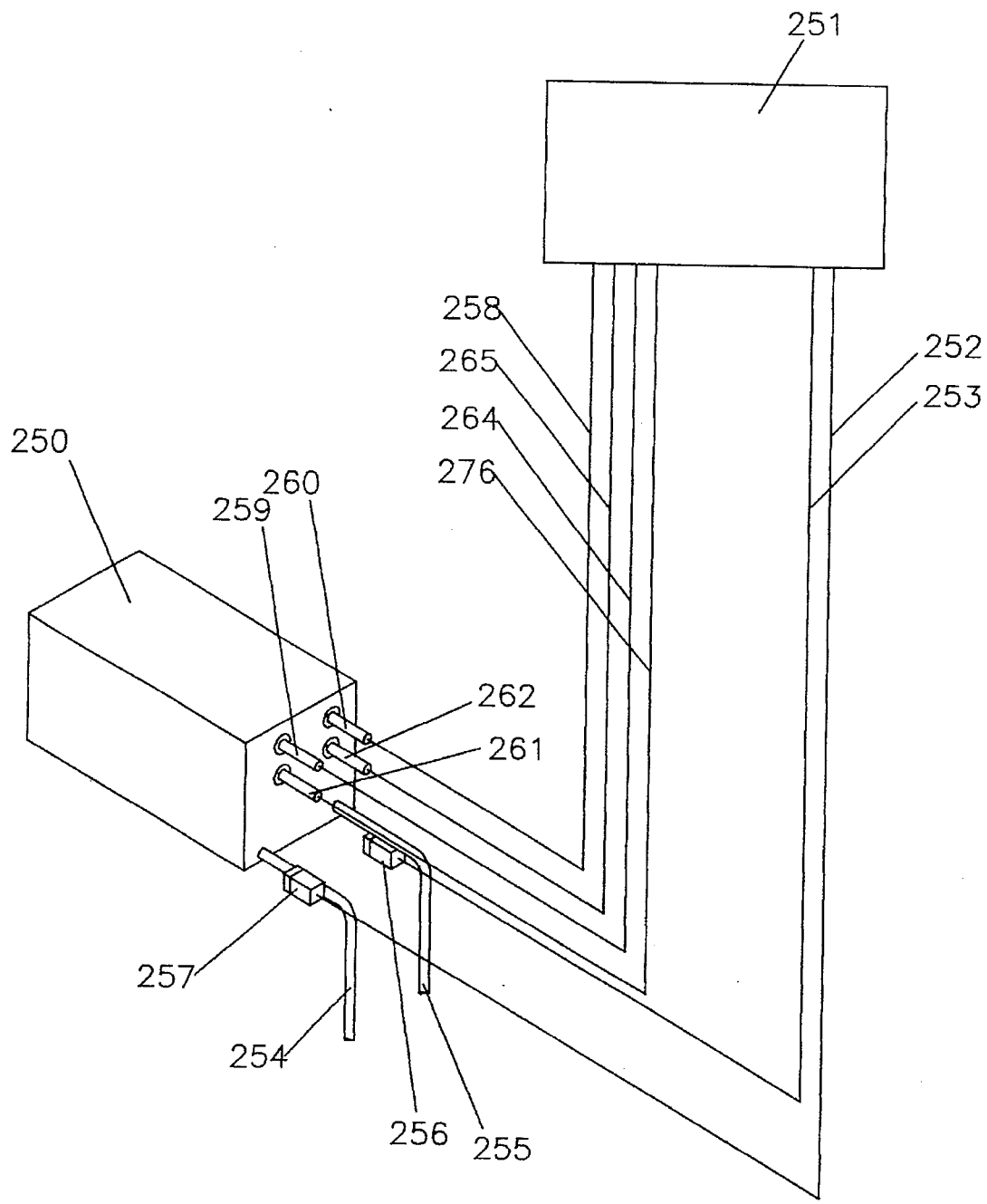
FIG. 6 sets forth one possible configuration in which the present invention is used in conjunction with a water level indicator.

The invention is configurable for use as a water level control. FIG. 6 sets forth a generalized diagram of the water purity testing system working as a fluid level control in its most basic configuration. The fluid level control system is generally referenced by numeral 263. The general system works with a tank 250 or reservoir to hold a liquid. The tank 250 contains two pipes, liquid in 255 and liquid out 254. With each entry and exit of fluid from the tank are controlled by valves 257 for exit and 256 for entry. Both valves 257 and 256 are connected by wires 252 and 253 which connect them to electronic control board 251. The electronic control board 251 uses the same DC current measurement balancing theories described in the water purity testing system to find out if there is water present in the tank 250. Instead of the electrodes being in a self-contained housing, they are placed into the sides or other places of the tank 250 and are connected by wires 258, 264, 265, and 266. The current design uses four electrodes 261, 262, 259, and 260. Electrodes 261 and 262 form the minimum level sense and electrodes 259 and 260 form the upper level sense. In this current design the water level is somewhere between the two grouping of electrodes. It is understood that other designs would include the use of two electrodes or other types of configurations. However, the method of measurement remains the same as in FIG. 2.

Further, the present invention can be configured for use as a probe used when testing solutions that coat, produce a film or when they can conduct across a non-conductive surface, and can also be used as a holding tank with level sense for these types of fluids.

Figure 7:
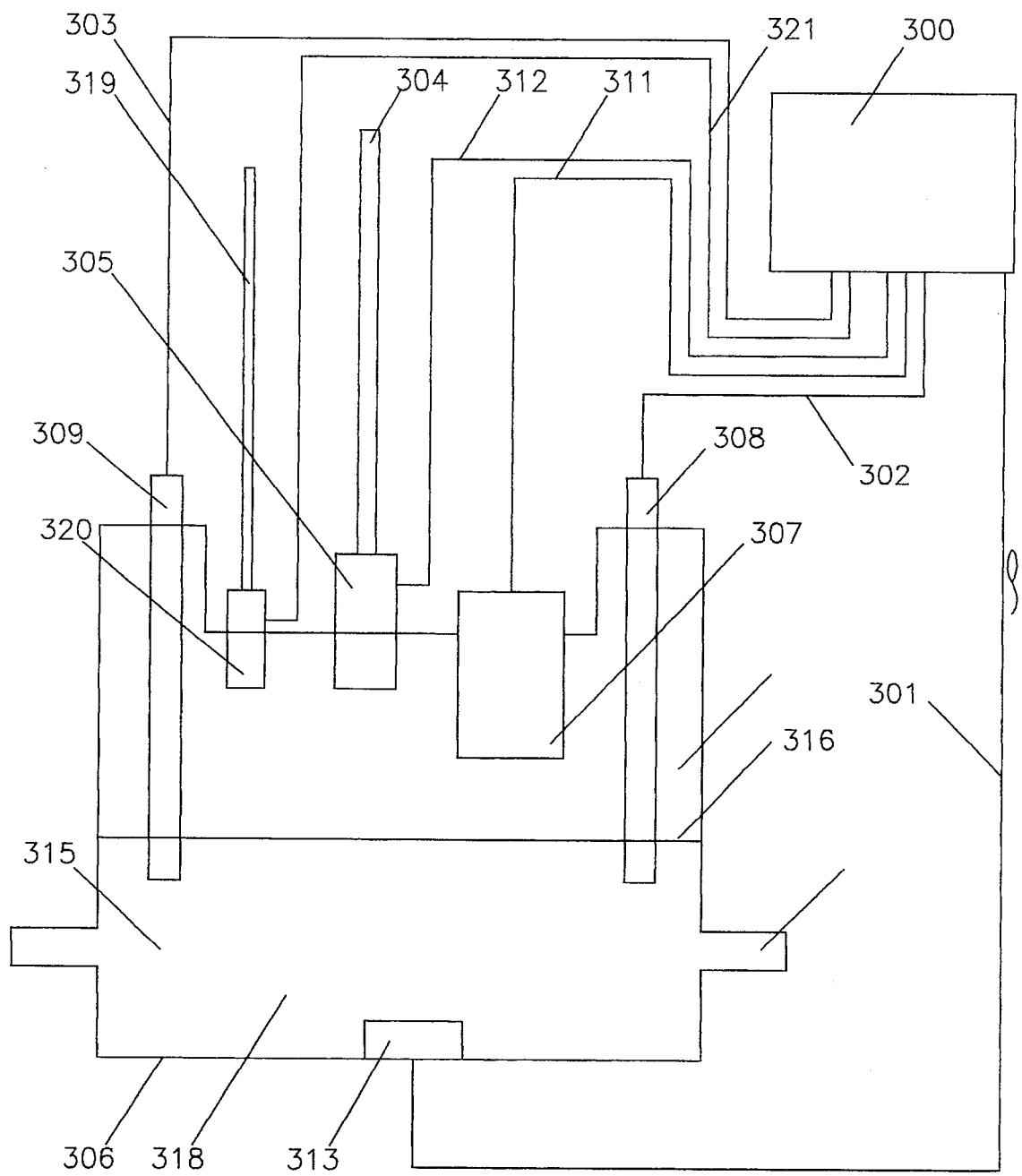
FIG. 7 sets forth one possible configuration in which the present invention is used in conjunction with a viscous materials coating device.

FIG. 7 sets forth a generalized diagram of the water purity sensing unit 315 when using testing solutions that coat, produce a film, or when they can conduct across a non-conductive surface when the fluid is drained. When trying to take a DC current measurement in the manner described in FIG. 2 on such fluids, the current invention must create an a barrier on which the solution 316 cannot rise enough in order to touch the top of the canister and leave a film between the electrodes 309 and 308 causing a false reading. This barrier can be air, CO2 or other gas and is numbered 317. In order to create this barrier by adding or exhausting a gas 317 is released into the sensor by valve 305 which is connected to pipe 304 from the place of origin and is also connected by wire 312 to the electronic circuit board 300. The gas is exhausted out of the sensor by valve 320 and through pipe 319 and is connected to the electronic circuit board 300 by wire 321. In order to regulate the level of fluid 316, a fluid level sensor 307 is used that is also connected by wire 311 to the electronic circuit board 300. The two electrodes 309 and 308 are connected by wires 303 and 310 to the electronic circuit board 300. And the temperature probe 313 is connected by wire 301 to the electronic circuit board 300. The sensing unit has a fluid input 315 which lets the fluid into the measurement area 318 and then a fluid output 314 where the fluid exits from. The unit is shaped with two raised upper cavities which contain the electrodes 309 and 308. The sensor is shaped this way so that in case the sensor is turned off or has a failure there will be two bubbles of gas which will protect the electrodes 309 and 308 until the problem can be fixed. It is understood that the different parts of the sensor unit can be rearranged and the size of the unit may vary and can be used as the sensor unit for FIGS. 1, 2, 3, 4, 5, and 6. Also, this sensor unit can act as a reservoir tank that uses electrodes 309 and 308 as top level sense and an enlarged lower casing 306 as the tank. It is understood that different numbers of electrodes could be used to indicate different levels inside the tank. However, the sensing would be done in the same DC current measurements as in FIG. 2.

While particular embodiments of the invention have been shown and described, it will be obvious to those skilled in the art that changes and modifications may be without departing from the invention in its broader aspects. Therefore, the aim in the appended claims is to cover all such changes and modifications as fall within the true spirit and scope of the invention.

What is claimed:

1. For use in testing water for dissolved solids, a water testing system comprising:

a pair of electrodes exposed to said water; and means for applying a voltage and current of predetermined magnitude, duration and first polarity to at least one of said electrodes and for measuring the current flow between said pair of electrodes during a first time period, and for grounding said first electrode to prevent the buildup of debris with respect to said electrodes, and for ungrounding said first electrode, and for applying a voltage and current of predetermined magnitude, duration and second polarity, opposite said first polarity, to said at least one electrode and for measuring the current flow between said pair of electrodes during a second time period period, and for grounding said first electrode to prevent the buildup of debris with respect to said electrodes, and for ungrounding said first electrode.

2. The water testing system recited in claim 1 and further comprising a housing, supporting said electrodes in a fixed relationship.

3. The water testing system recited in claim 2 wherein said housing is configured to facilitate the flow of water through said housing.

4. The water testing system recited in claim 1 and further comprising:

a temperature sensor for providing an indication of the magnitude of the temperature of said water;

computing means, electrically connected to said temperature sensor and said means for applying and measuring, for digitally storing a numeric representation of said current flow and said temperature.

5. The water testing system of claim 4 wherein said computing means is configured to determine a temperature factored total dissolved solids measurement based upon said temperature and said current flow.

6. For use in testing water for dissolved solids in the presence of a first and a second electrode of a two electrode system, a method comprising the steps of:

applying a constant voltage and a current to said first electrode;

measuring the current flow with respect to said first electrode based upon said applying said voltage and current to said first electrode step;

grounding said first electrode to prevent the build up of debris with respect to said electrodes;

ungrounding said first electrode;

applying a constant voltage and a current to said second electrode;

measuring the current flow with respect to said second electrode based upon said applying said voltage and current to said second electrode step; and grounding said second electrode to prevent the build up of debris with respect to said electrodes ungrounding said second electrode.

7. The method of claim 6 wherein said grounding of said first electrode is performed with respect to said second electrode and wherein said grounding of said second electrode is performed with respect to said first electrode.

8. The method of claim 6 wherein said grounding of said first electrode and said grounding of said second electrode is performed with respect to a third voltage reference.

9. The method of claim 6 wherein said water is available flowing through a conductive conduit, and said grounding of said first electrode and said grounding of said second electrode is performed with respect to said conductive conduit.

10. The method of claim 6 wherein said applying a voltage and current step is performed for a duration approximately equal to the duration of said grounding step.

11. The method of claim 6 and further comprising the step of measuring the temperature of said water.

12. The method of claim 11 and further comprising the step of displaying a representation of the total dissolved solids in said water based upon the temperature of said water and said current flow.

13. For use in testing water for dissolved solids in the presence of a first electrode and a second electrode of a two electrode system in contact with water, a method comprising the steps of:

applying a first voltage and current to said first electrode with respect to said second electrode;

measuring the current flow between said first and said second electrodes based upon said applying a first voltage and current step;

ceasing application of said first voltage and current to said first electrode;

applying a second voltage and current of substantially the same polarity of said first voltage and current to said second electrode with respect to said first electrode;

measuring the current flow between said second and said first electrodes based upon said applying a second voltage and current step;

ceasing application of said second voltage and current to said second electrode; and grounding said first electrode with respect to said second electrode to prevent the build up of debris with respect to said electrodes.

14. The method of claim 13 wherein said grounding of said first and said second electrodes are grounded with respect to a third voltage reference.

15. The method of claim 13 wherein said water is available flowing through a conductive conduit, and said grounding of said first electrode and said grounding of said second electrode is performed with respect to said conductive conduit.

16. The method of claim 13 wherein said applying a voltage and current step is performed for a duration approximately equal the duration of said grounding step.

17. A soft water indicator, including the water testing system of claim 1 wherein said pair of electrodes further comprises a first pair of electrodes and a second pair of electrodes and further comprising a soft water filter in fluid communication with said first and said second pair of electrodes.

18. For use in testing water for dissolved solids in the presence of a first and a second of electrode, a method comprising the steps of:

applying a constant voltage and a current of a first polarity to said first electrode; and measuring the current flow with respect to said first electrode based upon said applying said voltage and current of said first polarity to said first electrode step;

applying a constant voltage and a current of a second polarity, opposite to said first polarity, to said second electrode; and measuring the current flow with respect to said second electrode based upon said applying said voltage and current to said second electrode step;

and grounding said first electrode with respect to said second electrode after the occurrence of both of said applying a constant voltage and a current of said first polarity and said applying a constant voltage and current of said second polarity steps are completed, in order to remove debris from said first and said second electrodes.

* * * * *